US011110102B2

(12) United States Patent
Angulo Gonzalez

(10) Patent No.: US 11,110,102 B2
(45) Date of Patent: Sep. 7, 2021

(54) ANTIFUNGAL AGENTS USED IN COMBINATION

(71) Applicant: Scynexis, Inc., Jersey City, NJ (US)

(72) Inventor: David A. Angulo Gonzalez, Tampa, FL (US)

(73) Assignee: Scynexis, Inc., Jersey City, NJ (US)

( * ) Notice: Subject to any disclaimer, the term of this patent is extended or adjusted under 35 U.S.C. 154(b) by 0 days.

(21) Appl. No.: 15/945,428

(22) Filed: Apr. 4, 2018

(65) Prior Publication Data

US 2018/0325919 A1 Nov. 15, 2018

Related U.S. Application Data

(60) Provisional application No. 62/483,647, filed on Apr. 10, 2017.

(51) Int. Cl.
| | | |
|---|---|---|
| *A61K 31/58* | (2006.01) | |
| *A61K 31/506* | (2006.01) | |
| *A61K 31/4439* | (2006.01) | |
| *A61K 31/496* | (2006.01) | |
| *A61K 31/7048* | (2006.01) | |
| *A61P 31/10* | (2006.01) | |
| *A61K 31/4196* | (2006.01) | |
| *A61K 45/06* | (2006.01) | |

(52) U.S. Cl.
CPC .......... *A61K 31/58* (2013.01); *A61K 31/4196* (2013.01); *A61K 31/4439* (2013.01); *A61K 31/496* (2013.01); *A61K 31/506* (2013.01); *A61K 31/7048* (2013.01); *A61K 45/06* (2013.01); *A61P 31/10* (2018.01)

(58) Field of Classification Search
CPC ................ A61K 31/58; A61K 31/4196; A61K 31/4439; A61K 31/496; A61K 31/506; A61K 31/7048; A61K 45/06; A61P 31/10
See application file for complete search history.

(56) References Cited

U.S. PATENT DOCUMENTS

| 5,756,472 A | 5/1998 | Liesch et al. |
|---|---|---|
| 8,188,085 B2 | 5/2012 | Greenlee et al. |
| 2016/0207956 A1 | 7/2016 | Zhang |

FOREIGN PATENT DOCUMENTS

| WO | WO-2007/126900 A2 | 11/2007 | |
|---|---|---|---|
| WO | WO-2007/127012 A1 | 11/2007 | |
| WO | WO-2010/019203 A1 | 2/2010 | |
| WO | WO-2010/019204 A1 | 2/2010 | |
| WO | WO-2016/079536 A1 | 5/2016 | |
| WO | WO-2016079536 A1 * | 5/2016 | ........... A61K 31/496 |

OTHER PUBLICATIONS

Arikan et al., "In Vitro Synergy of Caspofungin and Amphotericin B against *Aspergillus* and *Fusarium* spp.," 46(1) Antimicrob. Agents Chemother. 245-47 (2002).
Buil et al., "Activity of F901318 against azole-resistant and difficult-to-treat *Aspergillus* species," 26th Eur. Congress Clin. Microbiol. Infect. Dis. P1605 (Apr. 2016).
Bundgaard (ed.), *Design of Prodrugs*, Elsevier (1985).
Clavaud et al., "The Composition of the Culture Medium Influences the β-1,3-Glucan Metabolism of *Aspergillus fumigatus* and the Antifungal Activity of β-1,3-Glucan Synthesis," 56(6) Antimicrob. Agents Chemother. 3428-31 (2012).
Elefanti et al., "Amphotericin B- and Voriconazole-Echinocandin Combinations against *Aspergillus* spp.: Effect of Serum on Inhibitory and Fungicidal Interactions," 57(10) Antimicrob. Agents Chemother. 4656-63 (2013).
Gennaro (ed.), *Remington: The Science and Practice of Pharmacy*, 20th edition (2000).
Marr et al., "Combination Antifungal Therapy for Invasive Aspergillosis: A Randomized Trial," 162 Ann. Intern. Med. 81-89 (2015).
Mukherjee et al., "Combination Treatment of Invasive Fungal Infections," 18(1) Clin. Microbiol. Rev. 163-94 (2005).
Odds, "Synergy, antagonism, and what the chequerboard puts between them," 52 J. Antimicrob. Chemother. 1 (2003).
Onishi et al., "Discovery of Novel Antifungal (1,3)-β-D-Glucan Synthase Inhibitors," 44(2) Antimicrob. Agents Chemother. 368-77 (2000).
Pelaez et al., "The Discovery of Enfumafungin, a Novel Antifungal Compound Produced by an Endophytic *Hormonema* Species: Biological Activity and Taxonomy of the Producing Organisms," 23(3) Syst. Appl. Microbiol. 333-43 (2000).
Perea et al., "In Vitro Interaction of Caspofungin Acetate with Voriconazole against Clinical Isolates of *Aspergillus* spp.," 46(9) Antimicrob. Agents Chemother. 3039-41 (2002).
Petraitis et al., "Combination Therapy in Treatment of Experimental Pulmonary Aspergillosis: Synergistic Interaction between an Antifungal Triazole and an Echinocandin," 187 J. Infect. Dis. 1834-43 (2003).
Pfaller et al., "In vitro activity of a Hos2 deacetylase inhibitor, MGCD290, in combination with echinocandins against echinocandin-resistant *Candida* species," 81 Diag. Microbiol. Infect. Dis. 259-63 (2015).
Philip et al., "In Vitro Synergy Testing of Anidulafungin with Itraconazole, Voriconazole, and Amphotericin B against *Aspergillus* spp. and *Fusarium* spp.," 49(8) Antimicrob. Agents Chemother. 3572-74 (2005).

(Continued)

*Primary Examiner* — Kortney L. Klinkel
*Assistant Examiner* — William Y Lee
(74) *Attorney, Agent, or Firm* — Covington & Burling LLP; Melody Lu; Jennifer L. Robbins

(57) ABSTRACT

The present invention relates to the use of enfumafungin derivative triterpenoid antifungal compounds in combination with other antifungal agents such azoles, polyenes, lipopeptides, and allylamides to treat fungal diseases. More particularly, the invention relates to antifungal combinations of enfumafungin derivative triterpenoids which are inhibitors of (1,3)-β-D-glucan synthesis, in combination with other antifungal agents such as mold-active agents that have activity against molds, including but not limited to voriconazole, isavuconazole, posaconazole, itraconazole and amphotericin B, for the treatment and/or prevention of infections caused by molds.

14 Claims, 3 Drawing Sheets

(56) References Cited

OTHER PUBLICATIONS

Schwartz et al., "Isolation and Structural Determination of Enfumafungin, a Triterpene Glycoside Antifungal Agent That Is a Specific Inhibitor of Glucan Synthesis," 122(16-20) J. Am. Chem. Soc. 4882-86 (2000).
Schwartz, "Cell wall active antifungal agents," 11(11) Exp. Opin. Ther. Patents 1761-72 (2001).
Siopi et al., "Dose optimization of voriconazole/anidulafungin combination against *Aspergillus fumigatus* using an in vitro pharmacokinectic/pharmacodynamic model and response surface analysis: clinical implications for azole-resistant aspergillus," 71 J. Antimicrob. Chemother. 3135-47 (2016).
Svetaz et al., "Antifungal drugs combinations: a patent review 2000-2015," 26(4) Exp. Opin. Ther. Patents 439-53 (2016).
International Search Report and Written Opinion, PCT/US2018/026088, dated Jul. 17, 2018.
Patterson et al., "Practice Guidelines for the Diagnosis and Management of Aspergillosis: 2016 Update by the Infectious Diseases Society of America," CID 63: e1-e60 (2016).

\* cited by examiner

ANTIFUNGAL AGENTS USED IN COMBINATION

FIELD OF THE INVENTION

The present invention relates to the use of enfumafungin derivative triterpenoid antifungal compounds in combination with other antifungal agents such azoles, polyenes, lipopeptides, and allylamides to treat fungal diseases. More particularly, the invention relates to antifungal combinations of enfumafungin derivative triterpenoids (or pharmaceutically acceptable salts thereof) which are inhibitors of (1,3)-β-D-glucan synthesis, in combination with other antifungal agents such as mold-active agents that have activity against molds, including but not limited to voriconazole, isavuconazole, posaconazole, itraconazole, and amphotericin B, for the treatment and/or prevention of infections caused by molds.

BACKGROUND OF THE INVENTION

Fungal infections caused by molds are a major healthcare problem with high associated mortality. Several molds, including *Aspergillus* species, Zygomycetes, *Fusarium* species, and *Scedosporium* species, can cause systemic fungal infections. Among these, *Aspergillus* spp. is the most common, accounting for approximately 85% of cases. Invasive pulmonary aspergillosis is a life-threatening infection for immunocompromised patients, with high mortality rates (20-40% range) despite the availability of antifungal agents with activity against the causative pathogen (*Aspergillus* spp.). The first recommended treatment option for invasive aspergillosis is mold-active azole antifungals (e.g., voriconazole, isavuconazole, posaconazole, and itraconazole). Amphotericin B formulations are a secondary option due to significant renal toxicity. Despite the availability of mold-active antifungals, treatment outcomes are not optimal, leading to frequent treatment failures and mortality.

In addition, there has been an emergence of azole-resistant *Aspergillus* species, further limiting therapeutic options for patients. Different and more effective treatment approaches are needed, and combination therapy may play an important role. Combination therapy, to be effective, should include antifungal agents that when administered together show a synergistic interaction that can potentially increase antifungal efficacy, reduce toxicity, cure faster, prevent or avoid the emergence of resistance, and/or provide broader-spectrum antifungal activity in comparison with monotherapy regimens. However, combination therapy may also be deleterious in the case of antagonistic interactions, decrease in antifungal efficacy, and increase in toxicity.

Enfumafungin is a hemiacetal triterpene glycoside that is produced in fermentations of a *Hormonema* spp. associated with living leaves of *Juniperus communis* (U.S. Pat. No. 5,756,472; Pelaez et al., *Systematic and Applied Microbiology*, 23:333-343, 2000; Schwartz et al., *JACS*, 122:4882-4886, 2000; Schwartz, R. E., *Expert Opinion on Therapeutic Patents*, 11(11):1761-1772, 2001). Enfumafungin is one of the several triterpene glycosides that have in vitro antifungal activities. The mode of the antifungal action of enfumafungin and other antifungal triterpenoid glycosides was determined to be the inhibition of fungal cell wall glucan synthesis by their specific action on (1,3)-β-D-glucan synthase (Onishi et al., *Antimicrobial Agents and Chemotherapy*, 44:368-377, 2000; Pelaez et al., *Systematic and Applied Microbiology*, 23:333-343, 2000). (1,3)-β-D-glucan synthase remains an attractive target for antifungal drug action because it is present in many pathogenic fungi and thereby affords broad antifungal spectrum; in addition, there is no mammalian counterpart, and consequently, these compounds have little or no mechanism-based toxicity. The triterpenoid compound derivatives of enfumafungin related to this invention have demonstrated activity against fungal isolates that are resistant to other glucan synthase inhibitors (e.g., lipopeptide agents such as echinocandins) indicating that the biological and molecular target of the enfumafungin derivatives is different from that of other glucan synthase inhibitors.

Various enfumafungin derivatives have been disclosed, e.g., in International Patent Publication Nos. WO 2007/126900 and WO 2007/127012.

Previous studies have evaluated the efficacy of other antifungal agents in combination for the treatment of *Aspergillus* spp. infections but have failed to conclusively demonstrate improved outcomes (Marr K, et al., Ann Intern Med. 2015; 162:81-89). These sub-optimal outcomes with combination therapy of available antifungals may be related to the lack of availability of oral formulations (e.g., for echinocandins and amphotericin B) limiting their long-term use (long-term use often being needed for the treatment of mold infections), and the emergence of resistance, particularly to azoles (the only agents available for oral and IV administration for *Aspergillus* infections). Other limitations of currently available antifungals for the treatment of mold infections include the high risk of drug-to-drug interactions of the azoles, and the renal toxicity associated with amphotericin B. There is a need in the art for antifungal combinations that provide improved cure and survival outcomes for fungal infections and that are suitable for long-term combination therapy, as needed for the treatment of mold infections. There is also a need in the art for safe and effective antifungal agents to be used in combination that may allow a reduction in the use of amphotericin B and azoles (e.g., by reduction of daily dosage or reduction of treatment duration), minimizing the risk of associated toxicities.

SUMMARY OF THE INVENTION

The present invention relates to enfumafungin derivatives used in combination with other mold-active antifungal agents for the treatment and/or prevention of mold infections. Enfumafungin derivatives, and pharmaceutically acceptable salts thereof, are useful in the inhibition of (1,3)-β-D-glucan synthase, and are useful in combination with other mold-active agents in the prevention or treatment of mycotic infections caused by one or more of various pathogens including but not limited to *Aspergillus, Mucor, Fusarium*, and *Scedosporium* species. The present invention addresses needs in the art such as those described above at least because the enfumafungin derivatives are active against azole-resistant *Aspergillus* strains, can be administered both intravenously and orally, and have very low risk for drug-to-drug interactions, and their use in the combinations described herein overcomes the limitations of other antifungal compounds and combinations.

The present invention provides combinations of (a) a compound of Formula (I), or a pharmaceutically acceptable salt thereof:

(I)

[Chemical structure of Formula (I)]

wherein:

X is O or H, H;

$R^e$ is $C(O)NR^fR^g$ or a 6-membered ring heteroaryl group containing 1 or 2 nitrogen atoms wherein the heteroaryl group is optionally mono-substituted on a ring carbon with fluoro or chloro or on a ring nitrogen with oxygen;

$R^f$, $R^g$, $R^6$ and $R^7$ are each independently hydrogen or $C_1$-$C_3$ alkyl;

$R^8$ is $C_1$-$C_4$ alkyl, $C_3$-$C_4$ cycloalkyl or $C_4$-$C_5$ cycloalkylalkyl;

$R^9$ is methyl or ethyl; and $R^8$ and $R^9$ are optionally taken together to form a 6-membered saturated ring containing 1 oxygen atom; and (b) a second antifungal agent, such as a mold-active agent having activity against molds, such as an antifungal azole compound or a polyene such as amphotericin B.

The invention also provides methods of treating or preventing fungal infection in patients using the compound of Formula (I) in combination with the second antifungal agent.

DETAILED DESCRIPTION OF THE INVENTION

Figure 1:
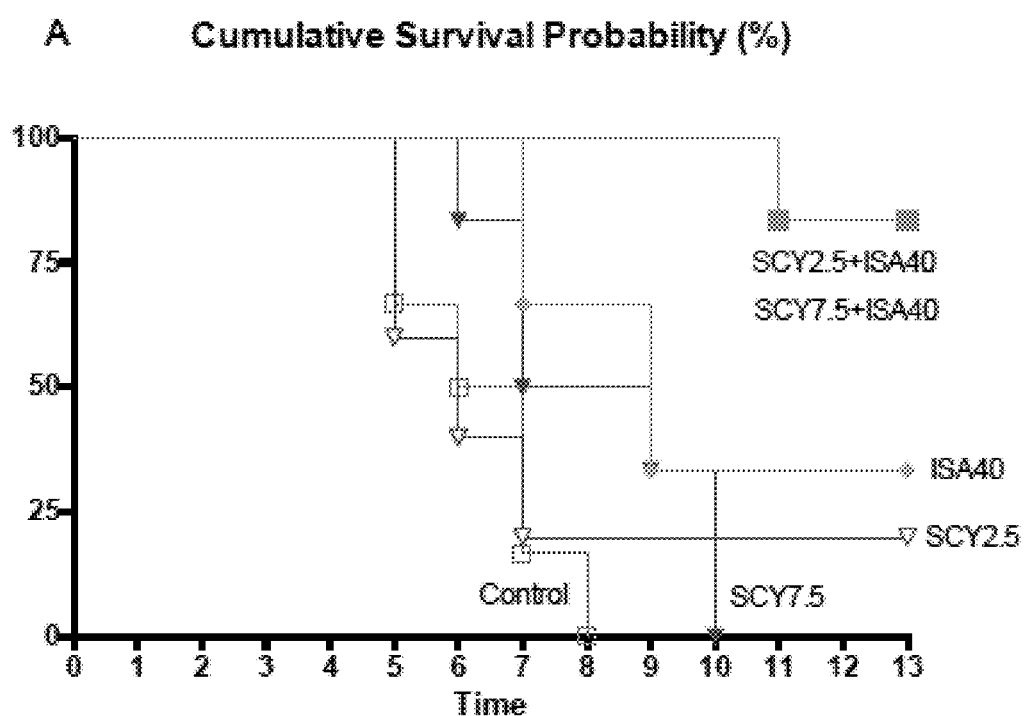
FIG. 1 is a graph showing cumulative survival probability from a study of New Zealand White rabbits inoculated with *Aspergillus fumigatus* isolate that were not treated with an antifungal agent (control), or were then treated with SCY-078 alone, with isavuconazole alone, or with a combination of SCY-078 and isavuconazole.

The present invention provides combinations of (a) a compound of Formula (I), or a pharmaceutically acceptable salt thereof:

(I)

[Chemical structure of Formula (I)]

wherein:

X is O or H, H;

$R^e$ is $C(O)NR^fR^g$ or a 6-membered ring heteroaryl group containing 1 or 2 nitrogen atoms wherein the heteroaryl group is optionally mono-substituted on a ring carbon with fluoro or chloro or on a ring nitrogen with oxygen;

$R^f$, $R^g$, $R^6$ and $R^7$ are each independently hydrogen or $C_1$-$C_3$ alkyl;

$R^8$ is $C_1$-$C_4$ alkyl, $C_3$-$C_4$ cycloalkyl or $C_4$-$C_5$ cycloalkylalkyl;

$R^9$ is methyl or ethyl; and $R^8$ and $R^9$ are optionally taken together to form a 6-membered saturated ring containing 1 oxygen atom; and (b) a second antifungal agent, such as a mold-active agent having activity against molds, such as an antifungal azole compound or a polyene such as amphotericin B.

The present invention also provides combinations of (a) a compound of Formula (Ia), or a pharmaceutically acceptable salt thereof:

(Ia)

[Chemical structure of Formula (Ia)]

wherein the substituents are as provided for in Formula (I); and (b) a second antifungal agent, such as a mold-active agent having activity against molds, such as an antifungal azole compound or a polyene such as amphotericin B.

In embodiment 1: X is H, H, and the other substituents are as provided for in Formula (I).

In embodiment 2: $R^e$ is either pyridyl or pyrimidinyl optionally mono-substituted on a ring carbon with fluoro or chloro or on a ring nitrogen with oxygen, and the other substituents are as provided in embodiment 1 or in Formula (I).

In embodiment 3: $R^e$ is 4-pyridyl and the other substituents are as provided in embodiment 1 or in Formula (I).

In embodiment 4: $R^e$ is $C(O)NH_2$ or $C(O)NH(C_1$-$C_3$ alkyl) and the other substituents are as provided in embodiment 1 or in Formula (I).

In embodiment 5: $R^8$ is $C_1$-$C_4$ alkyl and $R^9$ is methyl; and the other substituents are as provided in embodiment 1, 2, 3, or 4, or in Formula (I).

In embodiment 6: $R^8$ is t-butyl, $R^9$ is methyl; and the other substituents are as provided in embodiment 1, 2, 3, or 4, or in Formula (I).

In embodiment 7: $R^6$ and $R^7$ are each independently hydrogen or methyl and the other substituents are as provided in embodiment 1, 2, 3, 4, 5, or 6, or in Formula (I).

In embodiment 1': X is H, H, and the other substituents are as provided for in Formula (Ia).

In embodiment 2': $R^e$ is either pyridyl or pyrimidinyl optionally mono-substituted on a ring carbon with fluoro or chloro or on a ring nitrogen with oxygen, and the other substituents are as provided in embodiment 1' or in Formula (Ia).

In embodiment 3': $R^e$ is 4-pyridyl and the other substituents are as provided in embodiment 1' or in Formula (Ia).

In embodiment 4': $R^e$ is $C(O)NH_2$ or $C(O)NH(C_1-C_3$ alkyl) and the other substituents are as provided in embodiment 1' or in Formula (Ia).

In embodiment 5': $R^8$ is $C_1-C_4$ alkyl and $R^9$ is methyl; and the other substituents are as provided in embodiment 1', 2', 3', or 4', or in Formula (Ia).

In embodiment 6': $R^8$ is t-butyl, $R^9$ is methyl; and the other substituents are as provided in embodiment 1', 2', 3', or 4', or in Formula (Ia).

In embodiment 7': $R^6$ and $R^7$ are each independently hydrogen or methyl and the other substituents are as provided in embodiment 1', 2', 3', 4', 5', or 6', or in Formula (Ia).

In preferred embodiments, the present invention provides a combination of (a) a compound of Formula (II):

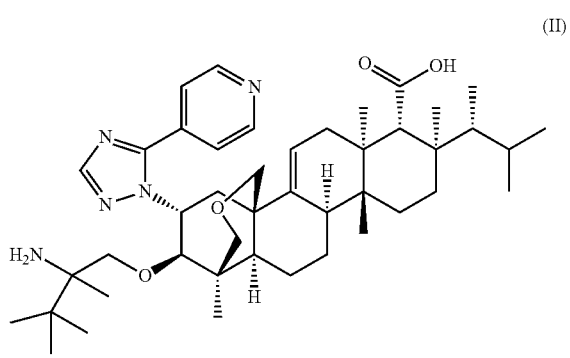

(II)

which is (1S,4aR,6aS,7R,8R,10aR,10bR,12aR,14R,15R)-15-[[2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid, or a pharmaceutically acceptable salt thereof; and (b) a second antifungal agent selected from voriconazole, isavuconazole, posaconazole, itraconazole, and amphotericin B.

In other preferred embodiments, the present invention provides a combination of (a) a compound of formula (IIa) (herein referred to as SCY-078):

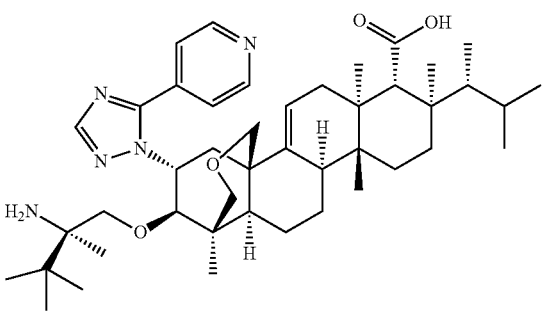

(IIa)

which is (1S,4aR,6aS,7R,8R,10aR,10bR,12aR,14R,15R)-15-[[(2R)-2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid, or a pharmaceutically acceptable salt thereof; and (b) a second antifungal agent selected from voriconazole, isavuconazole, posaconazole, itraconazole, and amphotericin B.

In other preferred embodiments, the present invention provides a combination of: the citrate salt of the compound of formula (II), and a second antifungal agent selected from voriconazole, isavuconazole, posaconazole, itraconazole and amphotericin B.

In other preferred embodiments, the present invention provides a combination of: the citrate salt of the compound of formula (IIa), and a second antifungal agent selected from voriconazole, isavuconazole, posaconazole, itraconazole, and amphotericin B.

Other embodiments of the present invention include the following:

(aa) A combination of: a composition comprising a compound of Formula (I), (Ia), (II), or (IIa), or a pharmaceutically acceptable salt thereof, and a carrier, adjuvant, or vehicle; and a second therapeutic agent.

(bb) A combination of: a pharmaceutical composition comprising a compound of Formula (I), (Ia), (II), or (IIa), or a pharmaceutically acceptable salt thereof, and a pharmaceutically acceptable carrier, adjuvant, or vehicle; and a second therapeutic agent.

(cc) The combination of (bb), wherein the second therapeutic agent is an azole, a polyene, a purine or pyrimidine nucleotide inhibitor, an orotomide, a Gwt1 inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent.

(dd) The combination of (cc), wherein the second therapeutic agent is itraconazole, ketoconazole, miconazole, fluconazole, voriconazole, posaconazole, amphotericin B, flucytosine, anidulafungin, micafungin, or caspofungin.

(ee) A pharmaceutical combination that is: a compound of Formula (I), (Ia), (II), or (IIa), or a pharmaceutically acceptable salt thereof; and a second therapeutic agent; wherein the compound (or the pharmaceutically acceptable salt thereof) and the second therapeutic agent are employed in amounts that render the combination effective for treating or preventing fungal and/or bacterial infections.

(ff) The combination of (ee), wherein the second therapeutic agent is an azole, a polyene, a purine or pyrimidine nucleotide inhibitor, an orotomide, a Gwt1 inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent.

(gg) The combination of (ff), wherein the second therapeutic agent is itraconazole, ketoconazole, miconazole, fluconazole, voriconazole, posaconazole, amphotericin B, flucytosine, anidulafungin, micafungin, or caspofungin.

(hh) A method of treating or preventing a mycotic infection in a subject in need thereof comprising administering to the subject a combination of: a first therapeutic agent that is a compound of Formula (I), (Ia), (II), or (IIa), or a pharmaceutically acceptable salt thereof; and a second therapeutic agent that is effective against a fungal and/or a bacterial infection.

(ii) The method of (hh), wherein the second therapeutic agent is an azole, a polyene, a purine or pyrimidine nucleotide inhibitor, an orotomide, a Gwt1 inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent.

(jj) The method of (hh), wherein the second therapeutic agent is itraconazole, ketoconazole, miconazole, fluconazole, voriconazole, posaconazole, amphotericin B, flucytosine, anidulafungin, micafungin, or caspofungin.

(kk) The method of (hh), wherein the first therapeutic agent is administered either sequentially or concurrently with the second therapeutic agent.

(ll) The method of (hh), wherein the therapeutic agents are administered intravenously, orally, and/or topically.

(mm) The method of (hh), wherein the mycotic infection is caused by Aspergillosis spp.

(nn) A method of treating or preventing invasive pulmonary aspergillosis in a subject in need thereof comprising administering to the subject a combination of: a first therapeutic agent that is a compound of Formula (I), (Ia), (II), or (IIa), or a pharmaceutically acceptable salt thereof; and a second therapeutic agent that is effective against a fungal and/or a bacterial infection.

(oo) The method of (nn), wherein the second therapeutic agent is an azole, a polyene, a purine or pyrimidine nucleotide inhibitor, an orotomide, a Gwt1 inhibitor, a pneumocandin or echinocandin derivative, a protein elongation factor inhibitor, a chitin inhibitor, a mannan inhibitor, a bactericidal/permeability-inducing (BPI) protein product, or an immunomodulating agent.

(pp) The method of (nn), wherein the second therapeutic agent is itraconazole, ketoconazole, miconazole, fluconazole, voriconazole, isavuconazole, posaconazole, amphotericin B, flucytosine, anidulafungin, micafungin, or caspofungin.

(qq) The method of (nn), wherein the first therapeutic agent is administered either sequentially or concurrently with the second therapeutic agent.

(rr) The method of (nn), wherein the therapeutic agents are administered intravenously, orally, and/or topically.

(ss) A method of treating a fungal and/or mold infection in a subject in need thereof, the method comprising administering to the subject a therapeutically effective amount of: a compound of Formula (I), (Ia), (II), or (IIa), or a pharmaceutically acceptable salt thereof, and a carrier, adjuvant, or vehicle; and a second antifungal agent, wherein the combination is synergistic.

The present invention also relates to methods of reducing the levels of galactomannan—a component of the cell wall of *Aspergillus* species—in a subject in need thereof, comprising administering to the subject a combination of: a first therapeutic agent that is a compound of Formula (I), (Ia), (II), or (IIa), or a pharmaceutically acceptable salt thereof; and a second therapeutic agent that is effective against a fungal and/or a bacterial infection. In certain embodiments, the first therapeutic agent is a compound of Formula (II) or a pharmaceutically acceptable salt thereof; and the second therapeutic agent is voriconazole, isavuconazole, posaconazole, itraconazole, or amphotericin B. In further embodiments, the first therapeutic agent is a compound of Formula (IIa) or a pharmaceutically acceptable salt thereof; and the second therapeutic agent is voriconazole, isavuconazole, posaconazole, itraconazole, or amphotericin B. Galactomannan levels in a subject can be determined, for example, by measuring galactomannan in serum or plasma from blood samples collected from the subject, or by bronchoalveolar lavage.

The present invention also includes any of the foregoing combinations: for use in, for use as a medicament for, or for use in the preparation of a medicament for treating or preventing a mycotic infection in a subject in need thereof; or for use in, for use as a medicament for, or for use in the preparation of a medicament for treating or preventing invasive pulmonary aspergillosis in a subject in need thereof.

In the description of compounds in the embodiments set forth above, indicated substitutions are included only to the extent that the substituents provide stable compounds consistent with the definition.

The compounds of Formula (I), (Ia), (II), and (IIa), and pharmaceutically acceptable salts and/or hydrate forms thereof, have antimicrobial (e.g., antifungal) activities against yeasts and other fungi, including one or more of *Acremonium*, *Absidia* (e.g., *Absidia corymbifera*), *Alternaria*, *Aspergillus* (e.g., *Aspergillus clavatus*, *Aspergillus flavus*, *Aspergillus fumigatus*, *Aspergillus nidulans*, *Aspergillus niger*, *Aspergillus terreus*, and *Aspergillus versicolor*), *Bipolaris*, *Blastomyces* (e.g., *Blastomyces dermatitidis*), *Blastoschizomyces* (e.g., *Blastoschizomyces capitatus*), *Candida* (e.g., *Candida albicans*, *Candida glabrata* (*Torulopsis glabrata*), *Candida guilliermondii*, *Candida kefyr*, *Candida krusei*, *Candida lusitaniae*, *Candida parapsilosis*, *Candida pseudotropicalis*, *Candida stellatoidea*, *Candida tropicalis*, *Candida utilis*, *Candida lipolytica*, *Candida famata* and *Candida rugosa*), *Cladosporium* (e.g., *Cladosporium carrionii* and *Cladosporium trichloides*), *Coccidioides* (e.g., *Coccidioides immitis*), *Cryptococcus* (e.g., *Cryptococcus neoformans*), *Curvularia*, *Cunninghamella* (e.g., *Cunninghamella elegans*), *Dermatophyte*, *Exophiala* (e.g., *Exophiala dermatitidis* and *Exophiala spinifera*), *Epidermophyton* (e.g., *Epidermophyton floccosum*), *Fonsecaea* (e.g., *Fonsecaea pedrosoi*), *Fusarium* (e.g., *Fusarium solani*), *Geotrichum* (e.g., *Geotrichum candidum* and *Geotrichum clavatum*), *Histoplasma* (e.g., *Histoplasma capsulatum* var. *capsulatum*), *Malassezia* (e.g., *Malassezia furfur*), *Microsporum* (e.g., *Microsporum canis* and *Microsporum gypseum*), *Mucor*, *Paracoccidioides* (e.g., *Paracoccidioides brasiliensis*), *Penicillium* (e.g., *Penicillium marneffei*), *Phialophora*, *Pityrosporum ovale*, *Pneumocystis* (e.g., *Pneumocystis carinii*), *Pseudallescheria* (e.g., *Pseudallescheria boydii*), *Rhizopus* (e.g., *Rhizopus microsporus* var. *rhizopodiformis* and *Rhizopus oryzae*), *Saccharomyces* (e.g., *Saccharomyces cerevisiae*), *Scedosporium* (e.g., *Scedosporium apiospermum*), *Scopulariopsis*, *Sporothrix* (e.g., *Sporothrix schenckii*), *Trichoderma*, *Trichophyton* (e.g., *Trichophyton mentagrophytes* and

*Trichophyton rubrum*), and *Trichosporon* (e.g., *Trichosporon asahii, Trichosporon beigelii* and *Trichosporon cutaneum*). The compounds are not only useful against organisms causing systemic human pathogenic mycotic infections, but also are useful against organisms causing superficial fungal infections such as *Trichoderma* sp. and other *Candida* spp. The compounds are particularly effective against *Aspergillus flavus, Aspergillus fumigatus, Candida albicans, Candida parapsilosis, Cryptococcus neoformans, Saccharomyces cerevisiae,* and *Trichophyton mentagrophytes.*

In view of their antifungal activity, compounds of Formula (I), (Ia), (II), and (IIa), and pharmaceutically acceptable salts and/or hydrate forms thereof, are useful for the treatment and/or prevention of one or more of a variety of superficial, cutaneous, subcutaneous and systemic mycotic infections in skin, eye, hair, nail, oral mucosa, gastrointestinal tract, bronchus, lung, endocardium, brain, meninges, urinary organ, vaginal portion, oral cavity, ophthalmus, systemic, kidney, bronchus, heart, external auditory canal, bone, nasal cavity, paranasal cavity, spleen, liver, hypodermal tissue, lymph duct, gastrointestine, articulation, muscle, tendon, interstitial plasma cell in lung, blood, and so on.

Therefore, compounds of Formula (I), (Ia), (II), and (IIa), and pharmaceutically acceptable salts and/or hydrate forms thereof, are useful for preventing and treating one or more of various infectious diseases, such as dermatophytosis (e.g., trichophytosis, ringworm or tinea infections), athletes foot, paronychia, *pityriasis versicolor*, erythrasma, intertrigo, fungal diaper rash, *candida* vulvitis, *candida* balanitis, otitis externa, candidiasis (cutaneous and mucocutaneous), chronic mucocandidiasis (e.g. thrush and vaginal candidiasis), cryptococcosis, geotrichosis, trichosporosis, aspergillosis, penicilliosis, fusariosis, zygomycosis, sporotrichosis, chromomycosis, coccidioidomycosis, histoplasmosis, blastomycosis, paracoccidioidomycosis, pseudallescheriosis, mycetoma, mycotic keratitis, otomycosis, pneumocystosis, and fungemia. The compounds may also be used as prophylactic agents to prevent systemic and topical fungal infections. Use as prophylactic agents may, for example, be appropriate as part of a selective gut decontamination regimen in the prevention of infection in immuno-compromised patients (e.g. AIDS patients, patients receiving cancer therapy or transplant patients). Prevention of fungal overgrowth during antibiotic treatment may also be desirable in some disease syndromes or iatrogenic states.

The compounds of Formula (I), (Ia), (II), and (IIa), and pharmaceutically acceptable salts and/or hydrate forms thereof, can be made according to the synthesis methods disclosed in U.S. Pat. No. 8,188,085, the contents of which are hereby incorporated by reference herein in their entirety.

Examples of azoles that may be used in combination with the compounds of Formula (I), (Ia), (II), and (IIa), and pharmaceutically acceptable salts and/or hydrate forms thereof, include but are not limited to: voriconazole, isavuconazole, itraconazole, ketoconazole, miconazole, ravuconazole, detoconazole, clotrimazole, and posaconazole. Examples of polyenes that may be used in combination with the compounds of Formula (I), (Ia), (II), and (IIa), and pharmaceutically acceptable salts and/or hydrate forms thereof, include but are not limited to: amphotericin B, nystatin, liposomal and lipid forms thereof such as ABELCET®, AMBISOME®, and AMPHOCIL®. Examples of purine or pyrimidine nucleotide inhibitors that may be used in combination with the compounds of Formula (I), (Ia), (II), and (IIa), and pharmaceutically acceptable salts and/or hydrate forms thereof, include but are not limited to: flucytosine or polyxins such as nikkomycines, in particular nikkomycine Z or nikkomycine X. Chitin inhibitors are another class of therapeutic agents that may be used in combination with the compounds of Formula (I), (Ia), (II), and (IIa), and pharmaceutically acceptable salts and/or hydrate forms thereof. Examples of elongation factor inhibitors that may be used in combination with the compounds of Formula (I), (Ia), (II), and (IIa), and pharmaceutically acceptable salts and/or hydrate forms thereof, include but are not limited to: sordarin and analogs thereof. Examples of orotomides that may be used in combination with the compounds of Formula (I), (Ia), (II), and (IIa), and pharmaceutically acceptable salts and/or hydrate forms thereof, include but are not limited to: F901318. Examples of Gwt1 inhibitors that may be used in combination with the compounds of Formula (I), (Ia), (II), and (IIa), and pharmaceutically acceptable salts and/or hydrate forms thereof, include but are not limited to: APX001. Examples of pneumocandin or echinocandin derivatives that may be used in combination with the compounds of Formula (I), (Ia), (II), and (IIa), and pharmaceutically acceptable salts and/or hydrate forms thereof, include but are not limited to: cilofungin, anidulafungin, micafungin, and caspofungin. Examples of mannan inhibitors that may be used in combination with the compounds of Formula (I), (Ia), (II), and (IIa), and pharmaceutically acceptable salts and/or hydrate forms thereof, include but are not limited to: predamycin. Examples of bactericidal/permeability-inducing (BPI) protein products that may be used in combination with the compounds of Formula (I), (Ia), (II), and (IIa), and pharmaceutically acceptable salts and/or hydrate forms thereof, include but are not limited to: XMP.97 and XMP.127. Examples of immunomodulators that may be used in combination with the compounds of Formula (I), (Ia), (II), and (IIa), and pharmaceutically acceptable salts and/or hydrate forms thereof, include but are not limited to: interferons (e.g., IL-1, IL-2, IL-3 and IL-8), defensines, tacrolimus and G-CSF (Granulocyte-colony stimulating factor).

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_1$-4 alkyl" refers to n-, iso-, sec- and t-butyl, n- and isopropyl, ethyl and methyl.

The term "cycloalkyl" refers to any cyclic ring of an alkane having a number of carbon atoms in the specified range. Thus, for example, "$C_3$-4 cycloalkyl" (or "$C_3$-$C_4$ cycloalkyl") refers to cyclopropyl and cyclobutyl.

The term "cycloalkyl-alkyl" (or equivalently "alkyl-cycloalkyl") as used herein refers to a system that includes an alkyl portion as described above and also includes a cycloalkyl portion as described above. Attachment to a "cycloalkyl-alkyl" (or "alkyl-cycloalkyl") may be through either the cycloalkyl or the alkyl portion. The specified number of carbon atoms in "cycloalkyl-alkyl" systems refers to the total number of carbon atoms in both the alkyl and the cycloalkyl parts. Examples of $C_4$-$C_5$ cycloalkyl-alkyl include but are not limited to methylcyclopropyl, dimethylcyclopropyl, methylcyclobutyl, ethylcyclopropyl, cyclopropylmethyl, cyclopropylethyl and cyclobutylmethyl.

The term "halogen" (or "halo") refers to fluorine, chlorine, bromine and iodine (alternatively referred to as fluoro, chloro, bromo, and iodo).

The term "or" as used herein denotes alternatives that may, where appropriate, be combined.

Unless expressly stated to the contrary, all ranges cited herein are inclusive. For example, a heterocyclic ring described as containing from "1 to 4 heteroatoms" means the ring can contain 1, 2, 3, or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

Any of the various cycloalkyl and heterocyclic/heteroaryl rings and ring systems defined herein may be attached to the rest of the compound at any ring atom (i.e., any carbon atom or any heteroatom) provided that a stable compound results. Suitable 5- or 6-membered heteroaromatic rings include, but are not limited to, pyridyl, pyrazinyl, pyrimidinyl, pyridazinyl and triazolyl.

A "stable" compound is a compound that can be prepared and isolated and whose structure and properties remain or can be caused to remain essentially unchanged for a period of time sufficient to allow use of the compound for the purposes described herein (e.g., therapeutic or prophylactic administration to a subject). Reference to a compound also includes stable complexes of the compound such as a stable hydrate.

As a result of the selection of substituents and substituent patterns, certain of the compounds of Formula (I), (Ia), (II), and (IIa) can have asymmetric centers and can occur as mixtures of stereoisomers, or as individual diastereomers, or enantiomers. Unless otherwise indicated, all isomeric forms of these compounds (and pharmaceutically acceptable salts and/or hydrate forms thereof), whether isolated or in mixtures, are within the scope of the present invention. Also included within the scope of the present invention are tautomeric forms of the compounds as depicted (and pharmaceutically acceptable salts and/or hydrate forms thereof).

When any variable occurs more than one time in any constituent or in Formula (I), (Ia), (II), or (IIa), its definition on each occurrence is independent of its definition at every other occurrence. Also, combinations of substituents and/or variables are permissible only if such combinations result in stable compounds.

The term "substituted" includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., an aryl, a cycloalkyl, a heteroaryl, or a heterocyclyl) provided such ring substitution is chemically allowed and results in a stable compound.

A bond terminated by a wavy line is used herein to signify the point of attachment of a substituent group or partial structure. This usage is illustrated by the following example:

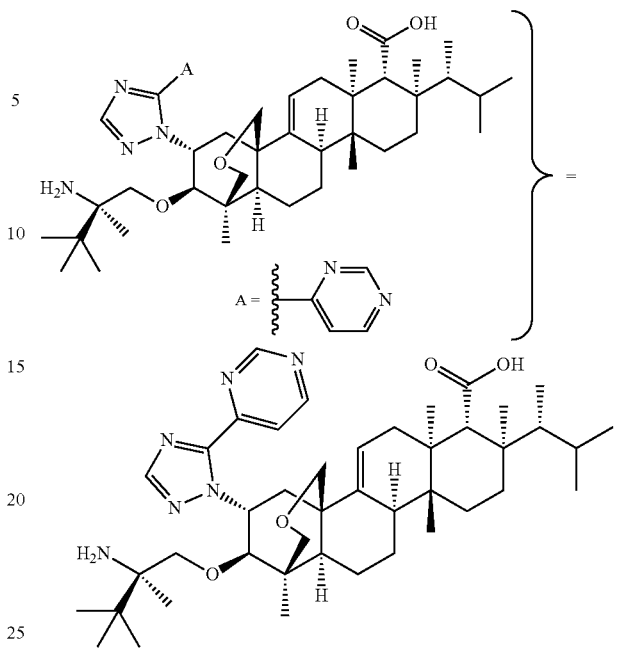

The compounds of Formula (I), (Ia), (II), and (IIa), and pharmaceutically acceptable salts and/or hydrate forms thereof, are also useful in the preparation and execution of screening assays for antifungal compounds. For example, the compounds are useful for isolating mutants, which are excellent screening tools for identifying further antifungal compounds.

The compounds of Formula (I), (Ia), (II), and (IIa) may be administered in the form of "pharmaceutically acceptable salts" or hydrates as appropriate. Other salts may, however, be useful in the preparation of the compounds or of their pharmaceutically acceptable salts. For example, when the compounds contain a basic amine group, they may be conveniently isolated as trifluoroacetic acid salts (e.g., following HPLC purification). Conversion of the trifluoroacetic acid salts to other salts, including pharmaceutically acceptable salts, may be accomplished by a number of standard methods known in the art. For example, an appropriate ion exchange resin may be employed to generate the desired salt. Alternatively, conversion of a trifluoroacetic acid salt to the parent free amine may be accomplished by standard methods known in the art (e.g., neutralization with an appropriate inorganic base such as $NaHCO_3$). Other desired amine salts may then be prepared in a conventional manner by reacting the free base with a suitable organic or inorganic acid. Representative pharmaceutically acceptable quaternary ammonium salts include the following: hydrochloride, sulfate, phosphate, carbonate, acetate, tartrate, citrate, malate, succinate, lactate, stearate, fumarate, hippurate, maleate, gluconate, ascorbate, adipate, gluceptate, glutamate, glucoronate, propionate, benzoate, mesylate, tosylate, oleate, lactobionate, laurylsulfate, besylate, caprylate, isetionate, gentisate, malonate, napsylate, edisylate, pamoate, xinafoate, napadisylate, hydrobromide, nitrate, oxalate, cinnamate, mandelate, undecylenate, and camsylate. Many of the compounds of Formula (I), (Ia), (II), and (IIa) carry an acidic carboxylic acid moiety, in which case suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The present invention includes within its scope the use of prodrugs of Formula (I), (Ia), (II), and (IIa). In general, such prodrugs will be functional derivatives of the compounds, which are readily convertible in vivo into the required compound. Thus, in the methods of treatment of the present invention, the term "administering" shall encompass the treatment of the various conditions described with the compound specifically disclosed or with a compound that converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of the compounds of Formula (I), (Ia), (II), and (IIa) include active species produced upon introduction of the compounds into the biological milieu.

The term "administration" and variants thereof (e.g., "administering" a compound) mean providing a compound or a prodrug of the compound to the subject in need of treatment. When a compound of Formula (I), (Ia), (II), and (IIa) or pharmaceutically acceptable salt thereof or a hydrate or prodrug thereof is provided in combination with a second active agent (e.g., other antifungal and/or antibacterial agents useful for treating fungal and/or bacterial infections), "administration" and its variants are each understood to include concurrent and sequential provision of the compound (or the salt, hydrate, or prodrug thereof) and of the other active agent.

As used herein, the term "composition" is intended to encompass a product comprising the specified ingredients, as well as any product that results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation, or experiment.

The term "synergistic" refers to the effect of a compound of Formula (I), (Ia), (II), or (IIa) or a pharmaceutically acceptable salt thereof or a hydrate or prodrug thereof provided in combination with a second active antifungal agent to prevent, manage, or treat a disorder, which effect is better or more beneficial or more pronounced than the additive effects of the individual therapies. A synergistic effect of a combination of therapies may permit the use of lower dosages of one or more of the individual therapies and/or less frequent administration of the therapies to a subject with a disorder. The ability to use lower dosages of a therapy and/or to administer the therapy less frequently reduces the toxicity associated with the administration of the therapy to a subject without reducing the efficacy of the therapy in the prevention or treatment of a disorder. In addition, a synergistic effect can result in improved efficacy of agents in the prevention or treatment of a disorder. Finally, a synergistic effect of a combination of therapies may permit avoidance or reduction of adverse or unwanted side effects associated with the use of either therapy alone.

The term "effective amount" as used herein means an amount of active ingredient or pharmaceutical agent that elicits the biological or medicinal response in a tissue, system, animal, or human that is being sought by a researcher, veterinarian, medical doctor, or other clinician. In one embodiment, the "effective amount" can be a therapeutically effective amount that alleviates the symptoms of the disease or condition being treated. In another embodiment, the "effective amount" can be a prophylactically effective amount for prophylaxis of the symptoms of the disease or condition being prevented or for reducing the likelihood of occurrence. The term can also refer to an inhibition effect amount of the enfumafungin derivative sufficient to inhibit (1,3)-β-D-glucan synthase and thereby elicit the response being sought. The term can also refer to the amount of the second antifungal agent, such as a mold-active agent, sufficient to inhibit the growth of the mold. The term can also refer to the amount of the enfumafungin derivative and the second agent that when administered in combination is sufficient to inhibit the growth of mold, and thereby elicit the response being sought (e.g., a therapeutically effective amount, a prophylactically effective amount, or an inhibition effective amount). When the enfumafungin derivatives and second antifungal agent are administered in a salt form, references to the amounts of these compounds are to the free acid or free base form of the compounds.

For the purpose of preventing or treating fungal infection, the combination therapy comprising a first antifungal agent that is compound of Formula (I), (Ia), (II), or (IIa) (optionally in the form of a salt or a hydrate) and a second antifungal agent can be administered in any way that that produces contact of the active agent with the agent's site of action. The first and second agents can be administered in conventional ways available for use in conjunction with pharmaceuticals, either as individual therapeutic agents or as a combination of therapeutic agents. They can be administered alone, but in accordance with a typical practice can be administered with a pharmaceutical carrier selected on the basis of the chosen route of administration and standard pharmaceutical practice. They can be administered simultaneously or sequentially for a portion of or for the entire duration of the antifungal regimen via any acceptable administration route appropriate for the intended purpose. For example: the first and second agents can be given intravenously, orally, or topically; or one intravenously and other orally; or one orally and other topically; or in any combination of administration routes as would be appropriate for the fungal infection being treated or prevented. For instance: in the case of invasive aspergillosis, the preferred route of administration will be intravenously and/or orally; for a skin fungal infection, the antifungal compounds can be administered both topically or one orally and other topically; for an ocular fungal infection, the antifungal agents can be administered both topically or one intravenously or orally and the other topically. For example, the compounds of Formula (I), (Ia), (II), and (IIa), and pharmaceutically salts and/or hydrate forms thereof and the second antifungal agent can be administered by one or more of the following routes: orally, parenterally (including subcutaneous injections, intravenous, intramuscular, intrasternal injection or infusion techniques), by inhalation (e.g., nasal or buccal inhalation spray, aerosols from metered dose inhalator, and dry powder inhalator), by nebulizer, ocularly, topically, transdermally, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose.

Further description of methods suitable for use in preparing pharmaceutical compositions and of ingredients suitable for use in said compositions is provided in *Remington's Pharmaceutical Sciences,* 20th edition, edited by A. R. Gennaro, Mack Publishing Co., 2000.

The compounds of Formula (I), (Ia), (II), and (IIa), and pharmaceutically acceptable salts and/or hydrate forms thereof, can be administered, e.g., orally or intravenously, in a dosage range of, for example, 0.001 to 1000 mg/kg of mammal (e.g., human) body weight per day in a single dose or in divided doses. An example of a dosage range is 0.01 to 500 mg/kg body weight per day orally or intravenously in a single dose or in divided doses. Another example of a dosage range is 0.1 to 100 mg/kg body weight per day orally or intravenously in single or divided doses. For oral administration, the compositions can be provided in the form of tablets or capsules containing, for example, 1.0 to 1000 milligrams of the active ingredient, particularly 1, 5, 10, 15, 20, 25, 50, 75, 100, 150, 200, 250, 300, 400, 500, 600, 750, and 1000 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The second antifungal agent, including but not limited to azoles or amphotericin B compounds, and their pharmaceutically acceptable salts and/or hydrate forms thereof, can be administered (e.g., orally or intravenously) in a dosage range of, for example, 0.001 to 1000 mg/kg of mammal (e.g., human) body weight per day in a single dose or in divided doses, more preferably in a dose range of 0.01 to 100 mg/kg. An example of a dosage range is 1 to 100 mg/kg body weight per day orally or intravenously in a single dose or in divided doses. Another example of a dosage range includes voriconazole administered at a range from 2 to 20 mg/kg per day orally or intravenously in single or divided doses. Another example of a dosage range includes amphotericin B administered at a range from 0.2 to 10 mg/kg per day intravenously in single or divided doses. For oral administration, the compositions can be provided in the form of (e.g.) tablets, suspensions, solutions or capsules containing, for example, 1.0 to 500 milligrams of the active ingredient, particularly 50, 75, 100, 150, 200, 250, 300, 375, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. For intravenous administration, the compositions can be provided in the form of (e.g.) solutions, suspensions or other acceptable pharmaceutical forms containing, for example, 1.0 to 500 milligrams of the active ingredient. For topical administration, the second antifungal agent can be provided as (e.g.) a cream, solution, ointment, foam, powder, lacquer, emulsion or other pharmaceutically acceptable forms containing, for example, 0.001 to 900 milligrams of the active ingredient per gram of product.

Antifungal activity of compounds can be demonstrated by various assays known in the art, for example, by their glucan synthesis inhibitory activity ($IC_{50}$), minimum inhibitory concentration (MIC) and minimum effective concentration (MEC) against filamentous molds and dermatophytes in a broth microdilution assay, or in vivo anti-*Aspergillus* activity in a mouse or rabbit models. The compounds of Formula (I) provided in the Examples of U.S. Pat. No. 8,188,085 were generally found to give an MEC against *Aspergillus fumigatus* in the range of <0.03-32 µg/mL.

EXAMPLES

The following examples serve only to illustrate the invention and its practice. The examples are not to be construed as limitations on the scope or spirit of the invention.
Combination Testing Interactions between different drugs are described variously as synergistic, indifferent, or antagonistic. Assessments of in vitro drug interactions are usually based on the "no interaction" theory, which assumes that drugs in combination do not interact with each other and are therefore considered indifferent. When the observed effect of the drug combination is more than that predicted from the "no interaction" theory, synergy is claimed. On the other hand, antagonism is claimed when the observed effect is less than that predicted.

To determine the type of interaction between a representative compound of the enfumafungin derivatives (SCY-078) with several antifungal agents against *Aspergillus fumigatus*, the most frequent mold causing invasive disease in humans, the checkerboard method was used. The citrate salt of the compound was used in the studies.

The checkerboard method involves the determination of percent growth inhibition of fungal cells in the presence of different combinations of drugs. Percent growth inhibition is calculated relative to growth in control wells which contain only cells and no drug. The assay was performed in 96-well microplates in which each row and each column contained twofold serial dilutions of drug A and drug B at concentrations ranging from 0 to slightly higher than their minimum inhibitory concentration (MIC). Each wall had a unique combination of the 2 drugs. Then the inoculum was added to each well and the growth was evaluated after 48 hrs incubation to determine the first well in which growth was inhibited. The checkerboard-based determination of MICs of antifungal agents in combination was followed by further analysis employing the nonparametric fractional inhibitory concentration index (FICI), which is defined by the following equation:

$$FICI = \left(\frac{MIC \text{ drug } A \text{ in combination}}{MIC \text{ drug } A}\right) + \left(\frac{MIC \text{ drug } B \text{ in combination}}{MIC \text{ drug } B}\right)$$

where MIC-A and MIC-B are the MICs of drugs A and B, respectively. According to the terminology of Odds (Odds, F. C. 2003. Synergy, antagonism, and what the chequerboard puts between them. J. Antimicrob. Chemother. 52:1), a FICI value of equal or lower than 0.5 is considered synergy, a FICI value of greater than 4.00 is considered antagonism, and a FICI value between greater than 0.5 to 4.0 is considered no interaction.

Each drug was initially diluted in either sterile, distilled water or in DMSO, depending on whether the drug was water-soluble or water-insoluble, respectively. Since SCY-078 is not soluble in water, a water-insoluble preparation was used.

Stock solution of SCY-078 was prepared in DMSO at 200 times the concentration desired for use in the drug plates. Serial dilutions of stock solution were conducted in DMSO to obtain eleven 2-fold dilutions of the drug. The SCY-078 solution was then diluted to 4 times the desired concentration in RPMI-1640 medium so that the DMSO would not limit growth of the organism and so that the quantity of DMSO was the same for every dilution.

Two 96-well plates are needed to conduct a combination test. Using a multichannel pipette, 50 µl of the lowest concentration of the first drug (Drug A) was added to each well of column 1 of the first plate (plate A) and column 1 of the second plate (plate B; rows A-D). Then, 50 µl of the next highest working dilution of Drug A was added to each well in column 2, continuing with dilutions until all columns 1-11 were filled. Column 12 was left empty. 50 µl of the lowest concentration of Drug B was added to each well in Row D of plate B. 50 µl of the next highest working dilution of Drug B was added to each well in row C of plate B, continuing with dilutions until all rows through row B of plate A were filled. Row A of plate A did not have any Drug B. 50 µl RPMI was added to row A and column 12 (well A-12 had 100 µl of straight RPMI).

Following the above, 100 µl of organism inoculum was added to every well. The plates were then incubated for 48 hours and visually read after incubation.

The objective of the study was to determine whether the combination of SCY-078 with voriconazole, isavuconazole, or amphotericin B would result in a combined in vitro antifungal activity exceeding the sum of the activities of each drug alone. Combination MIC testing was performed using the checkerboard assay described above.

Materials

Test Isolates:

The following six clinical strains of *Aspergillus* (4 wild-type and 2 resistant) were tested:

Wild-Type Strains

*A. fumigatus* MRL #20438

*A. fumigatus* MRL #28382

*A. fumigatus* MRL #28401

*A. fumigatus* MRL #28378

Resistant Strains

*A. fumigatus* MRL #28383

*A. fumigatus* MRL #28500

*A. fumigatus* 28500 has a CYP51 mutation at F46Y.

Antifungal Agents:

The following combinations were tested:

SCY-078+Voriconazole

SCY-078+Isavuconazole

SCY-078+Amphotericin B

*A. fumigatus* strains were obtained from the Mycology Reference Library (MRL) at Case Western Reserve University School of Medicine, Ohio, United States. SCY-078 was manufactured by Avista Laboratories, North Carolina, United States. Voriconazole, isavuconazole, and amphotericin B were sourced from commercial distributors.

Methods

Initial MIC determinations of the individual antifungals were performed according to the Clinical and Laboratory Standards Institute (CLSI) M38-A2 standard for the susceptibility testing of filamentous fungi.

Combination MIC testing was performed using a checkerboard test method according to the Center for Medical Mycology SOP A11.3. The checkerboard combination test method is a modification of the microdilution antifungal susceptibility test wherein two test compounds are combined in varying concentrations to determine whether they have synergistic, antagonistic, or no effect on the respective MIC values.

Antifungals were serially diluted two-fold in RPMI medium to produce eleven concentrations each and were combined in wells of a microtiter plate. Two rows consisting of serial dilutions of each individual drug were included. All combination testing was conducted in duplicate. Comparison of the MICs of the individual drugs to the MIC of the combined agents is indicative of their relative efficacy.

This interpretation followed the Antimicrobial Agents and Chemotherapy guidelines, which seek to encourage conservative interpretation of checkerboard combination data.

Results

Table 1 shows the FICI score and interpretation for SCY-078 in combination with isavuconazole against the azole sensitive and resistant *A. fumigatus* isolates tested (tests were run in duplicate). Against the susceptible isolates tested, the combination of SCY-078 and isavuconazole demonstrated synergy in in all four isolates tested. Against the resistant CYP51 mutant *A. fumigatus* strain 28500 and the resistant strain 28383, SCY-078 in combination with isavuconazole demonstrated no interaction.

Table 2 shows the FICI score and interpretation for SCY-078 in combination with voriconazole against the azole susceptible and resistant *A. fumigatus* isolates tested (tests were run in duplicate). Against the susceptible isolates tested, the combination of SCY-078 and voriconazole demonstrated synergy against all four isolates evaluated. The combination of SCY-078 and voriconazole showed no interaction when tested against the resistant *A. fumigatus* isolates.

Table 3 shows the FICI score and interpretation for SCY-078 in combination with amphotericin B against the azole susceptible and resistant *A. fumigatus* isolates tested (tests were run in duplicate). The combination of SCY-078 and amphotericin B demonstrated synergy against all the susceptible isolates evaluated. Against the resistant isolate, *A. fumigatus* 28383, SCY-078 in combination with amphotericin B showed no interaction. However, against the CYP51 mutant strain (*A. fumigatus* 28500), SCY-078 in combination with amphotericin B demonstrated synergistic activity.

TABLE 1

MIC values alone and in combination for SCY-078 and isavuconazole against *A. fumigatus* (μg/mL).
MICs were read at 48 hours and each test performed in duplicate.

| MRL | Organism | MIC per drug Alone | | MIC per drug in Combination | | FICI Score SCY-078/ | |
|---|---|---|---|---|---|---|---|
| | | SCY-078 | Isavuconazole | SCY-078 | Isavuconazole | Isavuconazole | Interpretation |
| 20438 | *A. fumigatus* | 4 | 1 | 0.016 | 0.5 | 0.50 | Synergistic |
| | | 4 | 1 | 0.016 | 0.5 | 0.50 | Synergistic |
| 28378 | *A. fumigatus* | 4 | 1 | 0.125 | 0.125 | 0.16 | Synergistic |
| | | 4 | 1 | 0.125 | 0.25 | 0.28 | Synergistic |
| 28382 | *A. fumigatus* | 8 | >8 | 0.016 | 0.25 | 0.03 | Synergistic |
| | | 4 | 1 | 0.063 | 0.25 | 0.27 | Synergistic |
| 28401 | *A. fumigatus* | 4 | 1 | 0.25 | 0.25 | 0.31 | Synergistic |
| | | 8 | 1 | 0.5 | 0.25 | 0.31 | Synergistic |
| *28383 | *A. fumigatus* | 4 | >8 | 0.063 | >8 | 1.02 | No interaction |
| | | 4 | >8 | 0.031 | 4 | 0.51 | No interaction |
| *28500 | *A. fumigatus* | 4 | >8 | 1 | >8 | 1.25 | No interaction |
| | | 4 | >8 | 0.125 | >8 | 1.03 | No interaction |

*Azole-resistant strains

TABLE 2

MIC values alone and in combination for SCY-078 and voriconazole against *A. fumigatus* (μg/mL).
MICs were read at 48 hours and each test performed in duplicate.

| MRL | Organism | MIC Alone | | MIC in Combination | | FICI Score SCY-078/ | |
|---|---|---|---|---|---|---|---|
| | | SCY-078 | Voriconazole | SCY-078 | Voriconazole | Voriconazole | Interpretation |
| 20438 | *A. fumigatus* | 8 | 1 | 0.125 | 0.25 | 0.27 | Synergistic |
| | | 4 | 1 | 0.25 | 0.25 | 0.31 | Synergistic |
| 28378 | *A. fumigatus* | 8 | 0.5 | 0.5 | 0.125 | 0.31 | Synergistic |
| | | 4 | 0.25 | 0.5 | 0.016 | 0.19 | Synergistic |
| 28382 | *A. fumigatus* | 8 | 0.5 | 0.5 | 0.125 | 0.31 | Synergistic |
| | | 8 | 0.5 | 0.016 | 0.25 | 0.50 | Synergistic |
| 28401 | *A. fumigatus* | 8 | 2 | 0.25 | 0.5 | 0.28 | Synergistic |
| | | 8 | 2 | 0.125 | 0.5 | 0.27 | Synergistic |
| *28383 | *A. fumigatus* | 8 | >16 | 0.031 | >16 | 1.00 | No interaction |
| | | 8 | >16 | 0.031 | >16 | 1.00 | No interaction |
| *28500 | *A. fumigatus* | 4 | >16 | 1 | >16 | 1.25 | No interaction |
| | | 8 | >16 | 1 | >16 | 1.13 | No interaction |

*Azole-resistant strains

TABLE 3

MIC values alone and in combination for SCY-078 and amphotericin B against *A. fumigatus* (μg/mL).
MICs were read at 48 hours and each test performed in duplicate.

| MRL | Organism | MIC Alone | | MIC in Combination | | FICI Score SCY-078/ | |
|---|---|---|---|---|---|---|---|
| | | SCY-078 | Amphotericin B | SCY-078 | Amphotericin B | Amphotericin B | Interpretation |
| 20438 | *A. fumigatus* | 4 | 4 | 0.016 | 0.5 | 0.13 | Synergistic |
| | | 4 | 4 | 0.016 | 0.5 | 0.13 | Synergistic |
| 28378 | *A. fumigatus* | 4 | 2 | 0.016 | 0.5 | 0.25 | Synergistic |
| | | 4 | 2 | 0.016 | 0.5 | 0.25 | Synergistic |
| 28382 | *A. fumigatus* | 4 | 4 | 0.016 | 1 | 0.25 | Synergistic |
| | | 8 | 4 | 0.063 | 0.5 | 0.13 | Synergistic |
| 28401 | *A. fumigatus* | 4 | 4 | 0.016 | 1 | 0.25 | Synergistic |
| | | 8 | 4 | 0.031 | 0.5 | 0.13 | Synergistic |
| *28383 | *A. fumigatus* | 4 | 4 | 0.016 | 4 | 1.00 | No interaction |
| | | 4 | 2 | 0.125 | 2 | 1.03 | No interaction |
| *28500 | *A. fumigatus* | 4 | 4 | 0.016 | 1 | 0.25 | Synergistic |
| | | 4 | 4 | 0.125 | 1 | 0.28 | Synergistic |

*Azole-resistant strains

These data show that combinations of SCY-078 and voriconazole, isavuconazole, and amphotericin B demonstrated synergistic activity against all of the wild-type *Aspergillus fumigatus* isolates tested. Combinations of SCY-078 and each of voriconazole, isavuconazole, and amphotericin B demonstrated either synergistic activity or no interaction against azole-resistant *Aspergillus fumigatus* isolates tested. Importantly, there was no antagonism demonstrated with these combinations.

In Vivo Study

A study was conducted to evaluate the efficacy of the combination of SCY-078 with isavuconazole. Isavuconazole is a second generation antifungal triazole with activity against *Aspergillus* spp. As described above, invasive pulmonary aspergillosis is a life-threatening infection in immunosuppressed patients—particularly those with severe and prolonged neutropenia as a consequence of myelotoxic chemotherapy for the treatment of cancer, and those receiving immunosuppressive medication for rejection prophylaxis after organ transplantation or treatment of graft-versus-host disease (GVHD) after allogeneic bone marrow transplantation. A neutropenic rabbit model was selected for this in vivo evaluation to further illustrate the effect of the combination therapy of SCY-078 and an azole, in a relevant immunosuppressed population.

Methods

New Zealand White rabbits weighing 2.5 to 3.5 kg (Covance Research Products, Inc., Denver, Pa.) were used in this study. Vascular access was established by the surgical placement of a silastic tunneled central venous catheter. Cytosine arabinoside (Cytosar-U) 525 mg/m$^2$ was administered intravenously on days 1 through 5, and on days 8, 9, 13 and 14 to produce profound and persistent neutropenia (a neutrophil concentration of <100 neutrophils/μL). Methylprednisolone (Solu-Medrol®, Pfizer, NY) 5 mg/kg was administered on days 1 through 3 to inhibit macrophage activity. Antibiotics (ceftazidime 75 mg/kg given intravenously twice daily; gentamicin 5 mg/kg given intravenously every other day; vancomycin 15 mg/kg given intravenously daily) were used for prevention of opportunistic bacterial infections during neutropenia.

Inoculum:

NIH *Aspergillus fumigatus* isolate 4215 (ATCC No. MYA-1163) obtained from a patient with a fatal case of pulmonary aspergillosis was used in this study. The *A. fumigatus* isolate was subcultured on potato dextrose agar slants (Remel Inc., Baltimore, Md.), incubated for 24 h at 37° C. and then kept at room temperature for 5 days prior to use. On day 2 (i.e., 1 day after the first dose of cytosine arabinoside), under direct visualization, the inoculum (2.5×10$^8$ *A. fumigatus* conidia) was administered beyond the vocal cords into the trachea.

Antifungal Therapy:

As outlined in Table 4, the following six treatment groups were studied: a group receiving SCY-078 at 2.5 mg/kg/day (SCY2.5); a group receiving SCY-078 at 7.5 mg/kg/day (SCY7.5); a group receiving isavuconazole at 40 mg/kg/day (ISA40); a group receiving SCY-078 at 2.5 mg/kg/day and isavuconazole at 40 mg/kg/day (SCY2.5+ISA40); a group receiving SCY-078 at 7.5 mg/kg/day and isavuconazole at 40 mg/kg/day (SCY7.5+ISA40); and an untreated control group (UC). Each group included six rabbits. The antifungal agents, where administered, were administered intravenously once a day. The citrate salt of SCY-078 was used. In the groups receiving antifungal therapy, such administration started 24 h after the endotracheal inoculation and was continued once daily for 12 days. Surviving rabbits in the treated groups were sacrificed 24 h after the last administration of antifungal agent(s). No animals in the untreated group survived past day 8.

Evaluations:

Survival, pulmonary infarct, and galactomannan antigenemia (a serological marker of *Aspergillus* infection) were evaluated as indicators of treatment response. After death or sacrifice, the lungs were weighed and inspected by two blinded observers for the presence of lesions of hemorrhagic infarction typical of pulmonary aspergillosis. Blood from each rabbit was collected every other day for determination of serum galactomannan concentrations. Serum galactomannan concentrations were determined by the Platelia® *Aspergillus* enzyme immunoassay (EIA) (Bio-Rad, Marnes-la-Coquette, France) one-stage immunoenzymatic sandwich microplate assay method. Enzyme immunoassay data were expressed as a serum GMI (galactomannan index) plotted over time.

TABLE 4

| | Treatment Groups | | |
|---|---|---|---|
| Group No. | Treatment Group | Dosage (mg/kg/day) | Number of animals |
| 1 | Untreated Control (UC) | 0 | 6 |
| 2 | SCY2.5 | 2.5 | 6 |
| 3 | SCY7.5 | 7.5 | 6 |
| 4 | ISA40 | 40 | 6 |
| 5 | SCY2.5 + ISA40 | 2.5 and 40 | 6 |
| 6 | SCY7.5 + ISA40 | 7.5 and 40 | 6 |
| Total | | | 36 |

Results

Figure 2:
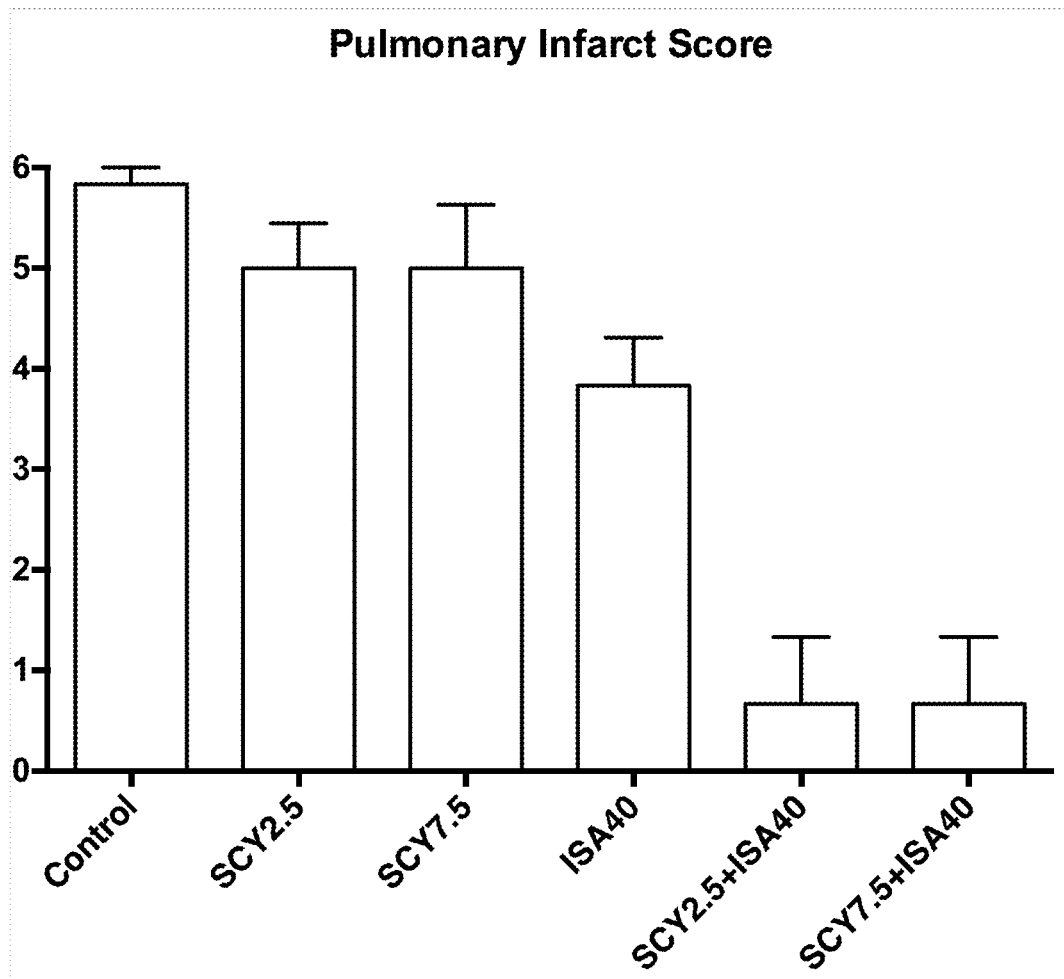
FIG. 2 is a graph showing pulmonary infarct scores from the study referenced in FIG. 1.
Figure 3:
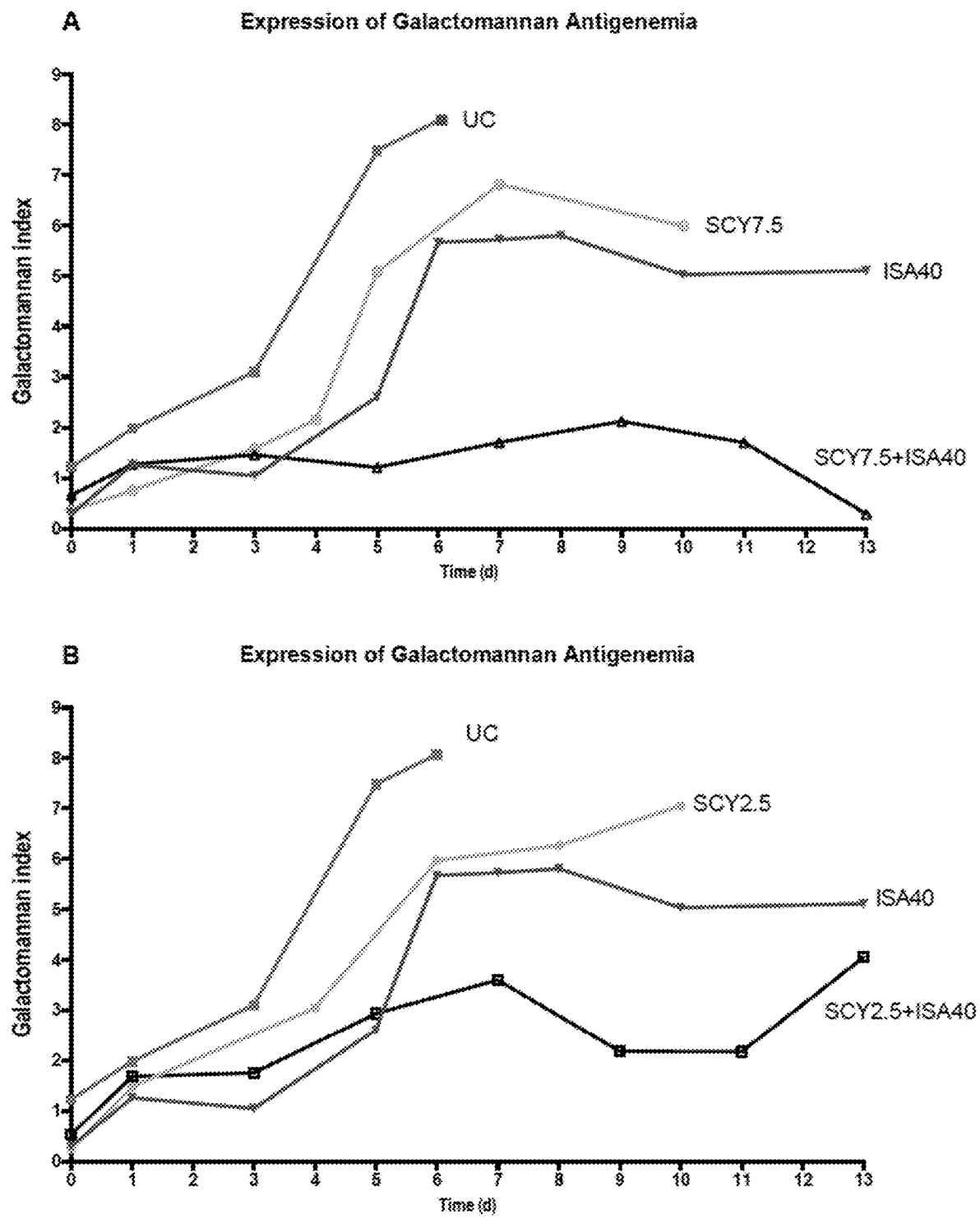
FIG. 3 is a graph showing galactomannan antigen levels detected in serum from the rabbits from the study referenced in FIG. 1.

Survival was significantly increased in animals treated with SCY7.5+ISA40 or SCY2.5+ISA40 in comparison to those receiving only SCY-078 (SCY7.5 or SCY2.5) or only isavuconazole (ISA40) (FIG. 1). Specifically, the rabbits receiving SCY7.5+ISA40 or SCY2.5+ISA40 had a survival rate, up to the day of scheduled sacrifice (day 13), of 83% (5 out of 6 in each group), whereas the animals receiving only ISA40 had a survival rate of 32% (2 out of 6); the animals receiving only SCY2.5 had a survival rate of 16% (1 out of 6); and the animals receiving only SCY7.5 and untreated controls had no animals surviving until day 13. The markers of pulmonary injury (pulmonary infarct score) demonstrated a similar pattern of response (FIG. 2). Serum galactomannan antigenemia was noticeably reduced in animals treated with SCY7.5+ISA40 or SCY2.5+ISA40 in comparison to those treated with single agents (FIG. 3). The combination of SCY-078 and isavuconazole was more effective in reducing galactomannan levels than either agent by itself. Moreover, the combination of SCY-078 and isavuconazole provided a faster decline in galactomannan antigenemia than either agent by itself.

This study further showed that the combination of SCY-078 with an azole was more efficacious and exhibited synergistic effect in treating invasive pulmonary aspergillosis as compared with either SCY-078 or the azole alone, in this model.

While this invention has been particularly shown and described with references to preferred embodiments thereof, it will be understood in light of the present disclosure by those skilled in the art that various changes in form and details may be made therein without departing from the scope of the invention encompassed by the appended claims.

What is claimed is:

1. A method of treating an *Aspergillus* infection in a subject in need thereof, the method comprising administering to the subject:
(a) a first therapeutic agent that is a compound of Formula (II):

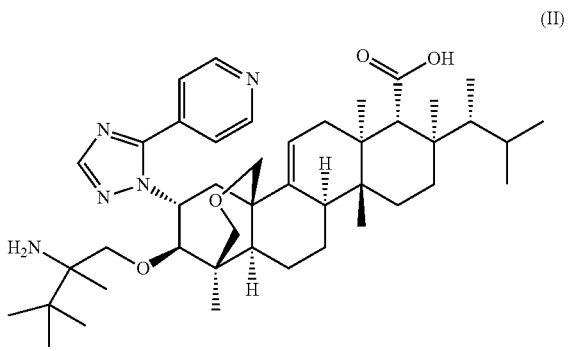

(II)

which is (1S,4aR,6aS,7R,8R,10aR,10bR,12aR,14R,15R)-15-[[2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid,
or a pharmaceutically acceptable salt thereof; and
(b) a second therapeutic agent that is isavuconazole,
wherein the first therapeutic agent is administered orally at a dose of 50 mg to 1000 mg, and the second therapeutic agent is administered at a dose of 50 mg to 1000 mg, and
wherein the dose of the first therapeutic agent and the dose of the second therapeutic agent are each administered at least once or twice per day for at least one week.

2. The method according to claim 1, wherein the *Aspergillus* infection is invasive pulmonary aspergillosis.

3. A method of treating an *Aspergillus* infection in a subject in need thereof, the method comprising administering to the subject:
(a) a first therapeutic agent that is a compound of Formula (IIa):

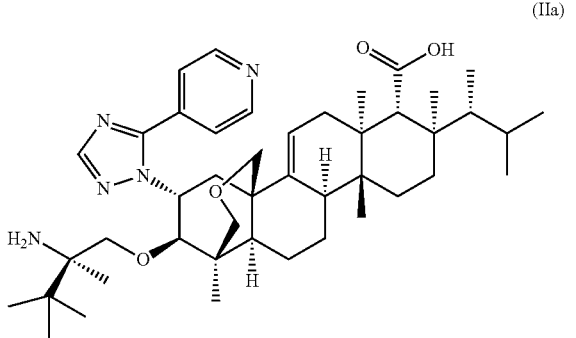

(IIa)

which is (1S,4aR,6aS,7R,8R,10aR,10bR,12aR,14R,15R)-15-[[2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylicacid,
or a pharmaceutically acceptable salt thereof; and
(b) a second therapeutic agent that is isavuconazole,
wherein the first therapeutic agent is administered orally at a dose of 50 mg to 1000 mg, and the second therapeutic agent is administered at a dose of 50 mg to 1000 mg, and
wherein the dose of the first therapeutic agent and the dose of the second therapeutic agent are each administered at least once or twice per day for at least one week.

4. The method according to claim 3, wherein the *Aspergillus* infection is invasive pulmonary aspergillosis.

5. The method according to claim 3, wherein the first therapeutic agent is the citrate salt of the compound of Formula (IIa).

6. The method according to claim 3, wherein the first therapeutic agent is administered sequentially with the second therapeutic agent.

7. The method according to claim 3, wherein the first therapeutic agent is administered concurrently with the second therapeutic agent.

8. A method of preventing pulmonary aspergillosis in a subject in need thereof, the method comprising administering to the subject:
(a) a first therapeutic agent that is a compound of Formula (IIa):

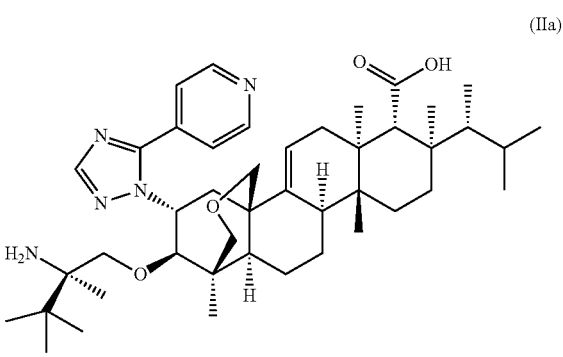

(IIa)

which is (1S,4aR,6aS,7R,8R,10aR,10bR,12aR,14R,15R)-15-[[2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylic acid,
or a pharmaceutically acceptable salt thereof, and
(b) a second therapeutic agent that is isavuconazole,
wherein the first therapeutic agent is administered orally at a dose of 50 mg to 1000 mg, and the second therapeutic agent is administered at a dose of 50 mg to 1000 mg, and
wherein the dose of the first therapeutic agent and the dose of the second therapeutic agent are each administered at least once or twice per day for at least one week.

9. A method of treating an *Aspergillus* infection in a subject in need thereof, the method comprising administering to the subject:
(a) a first therapeutic agent that is a compound of Formula (IIa):

(IIa)

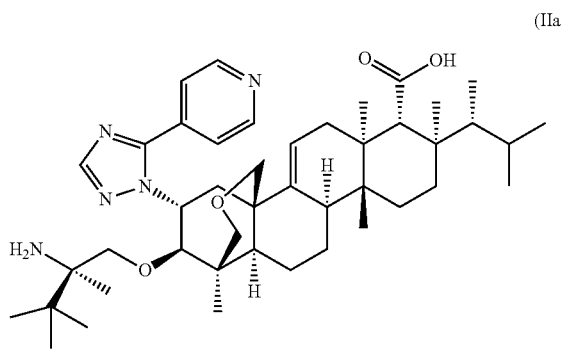

which is (1S,4aR,6aS,7R,8R,10aR,10bR,12aR,14R,15R)-15-[[2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylicacid, or a pharmaceutically acceptable salt thereof; and (b) a second therapeutic agent that is isavuconazole, wherein the first therapeutic agent and the second therapeutic agent are each administered in an amount effective to increase survival compared to the survival resulting from the administration of the first therapeutic agent in the absence of the second therapeutic agent or the administration of the second therapeutic agent in the absence of the first therapeutic agent.

10. The method according to claim 9, wherein the *Aspergillus* infection is invasive pulmonary aspergillosis.

11. A method of treating an *Aspergillus* infection in a subject in need thereof, the method comprising administering to the subject a pharmaceutical combination of:

(a) a first therapeutic agent that is a compound of Formula (IIa):

(IIa)

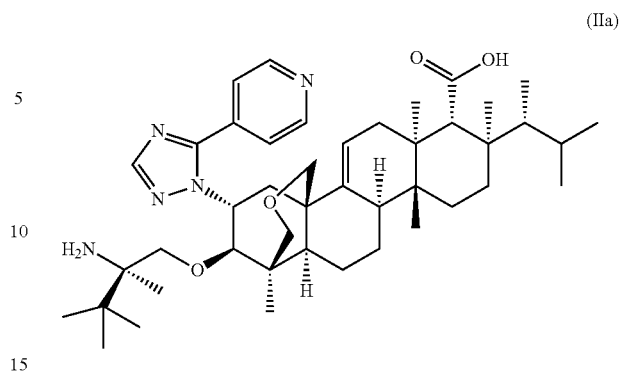

which is (1S,4aR,6aS,7R,8R,10aR,10bR,12aR,14R,15R)-15-[[2-amino-2,3,3-trimethylbutyl]oxy]-8-[(1R)-1,2-dimethylpropyl]-14-[5-(4-pyridinyl)-1H-1,2,4-triazol-1-yl]-1,6,6a,7,8,9,10,10a,10b,11,12,12a-dodecahydro-1,6a,8,10a-tetramethyl-4H-1,4a-propano-2H-phenanthro[1,2-c]pyran-7-carboxylicacid, or a pharmaceutically acceptable salt thereof, and (b) a second therapeutic agent that is isavuconazole, wherein the pharmaceutical combination, when administered to a first population of subjects having an *Aspergillus* infection, results in a survival rate that is higher than the survival rate of a second population of subjects having an *Aspergillus* infection and receiving either (i) the first therapeutic agent or (ii) the second therapeutic agent.

12. The method according to claim 11, wherein the *Aspergillus* infection is invasive pulmonary aspergillosis.

13. The method according to claim 11, wherein administering to the subject the pharmaceutical combination comprises administering the first therapeutic agent sequentially with the second therapeutic agent.

14. The method according to claim 11, wherein administering to the subject the pharmaceutical combination comprises administering the first therapeutic agent concurrently with the second therapeutic agent.

* * * * *